| United States Patent [19] | [11] | 4,153,722 |
|---|---|---|
| Campbell et al. | [45] | May 8, 1979 |

[54] METHOD OF TREATMENT

[75] Inventors: Henry F. Campbell, Lansdale; Norman J. Santora, Roslyn; George H. Douglas, Malvern, all of Pa.

[73] Assignee: William H. Rorer, Inc., Fort Washington, Pa.

[21] Appl. No.: 839,961

[22] Filed: Oct. 6, 1977

[51] Int. Cl.$^2$ ............................................. A61U 31/275
[52] U.S. Cl. ..................................................... 424/304
[58] Field of Search ......................................... 424/304

[56] References Cited

U.S. PATENT DOCUMENTS 3,279,907  10/1966  Lindner .................................. 71/2.3

Primary Examiner—Stanley J. Friedman

[57] ABSTRACT

This invention describes a method of treating inflammation in warmblooded animals by topically administering an effective amount of α-phenyl-N-phenylnitrone and derivatives thereof.

4 Claims, No Drawings

METHOD OF TREATMENT

SUMMARY OF THE INVENTION

This invention describes the pharmaceutical compositions and method of treating warmblooded animals for the relief of inflammation and associated pain and fever by the topical administration of α-phenyl-N-phenylnitrone and its derivatives.

BACKGROUND OF THE INVENTION

Continuous studies have been carried out during the last decade to develop drugs which would significantly inhibit the development of inflammation and relief of pain as well as the pain and fever associated with it. While much of this effort has been carried out in the steroidal field, there have been compounds developed with are non-steroidal such as the alkanoic acids derived from biphenyl, stilbene, naphthalene and various heteryl rings. While many of these compounds have been found to be effective, they have had the drawback of causing various side effects or being effective only on a specific disorder.

We have unexpectedly found that the α-phenyl-N-phenylnitrone and its derivatives have pharmacological properties which are useful for the relief and inhibition and prevention of inflammation conditions when administered topically.

We have also found that these compounds are effective in the treatment of inflammation and control of arthritic conditions associated with inflammation.

DESCRIPTION AND PREFERRED EMBODIMENTS

This invention describes a new method of treating inflammation in warmblooded animals by the topical administration of a compound having the structural formula as shown in FIG. 1.

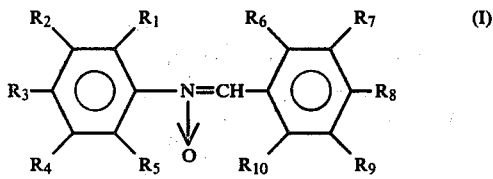

(I)

where:
R$_1$, R$_2$, Rhd 3, R$_4$, R$_5$, R$_6$, R$_7$, R$_8$, R$_9$, and R$_{10}$ may be the same or different and are:
hydrogen,
alkyl,
cyano,
nitro,
amino,
haloloweralkoxy,
haloloweralkyl,
halo,
loweralkoxy,
acyl,
acyloxy,
thio,
acylthio,
loweralkylthio,
loweralkylsulfinyl,
loweralkylsulfonyl and
hydroxy.

R$_3$ and R$_8$ may also be cycloalkyl, cycloalkenyl, aryl and heteroloweralkylidenyl.

The more preferred compounds for a method of topically treating inflammation embrace those compounds of the Formula II:

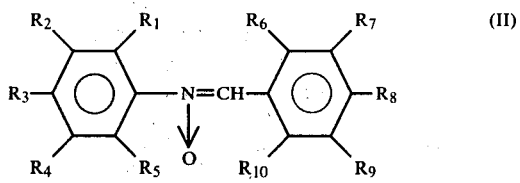

(II)

where:
R$_1$, R$_2$, R$_4$, R$_5$, R$_6$, R$_7$, R$_g$ and R$_{10}$ are
hydrogen,
alkyl,
alkoxy,
halo,
haloloweralkyl and
hydroxy;
R$_3$ and R$_8$ are
hydrogen,
alkyl,
alkoxy,
halo,
haloloweralkyl,
hydroxy,
phenyl and
cyclohexyl.

In the descriptive portions of this invention the following definitions apply:

"alkyl" refers to a loweralkyl hydrocarbon group containing from 1 to about 7 carbon atoms which may be straight chained or branched;

"alkenyl" refers to an unsaturated or partially unsaturated hydrocarbon group containing from 2 to about 7 carbon atoms which may be straight chained or branched;

"cycloalkyl" refers to a hydrocarbon ring having up to about 7 carbon atoms;

"cycloalkenyl" refers to a partially unsaturated hydrocarbon ring having up to about 7 carbon atoms;

"aryl" refers to any benzenoid aromatic group but preferably phenyl;

"acyl" refers to any organic radical derived from an organic acid by the removal of its hydroxyl group such as formyl, acetyl, propionyl, 3-carboxy-2-propenoyl, camphoryl, benzoyl, toluoyl or heteroyl such as pyridinoyl, piperidonyl, thenoyl, etc.

"alkoxy" refers to a loweralkoxy group containing from 1 to about 6 carbon atoms which may be straight chained or branched;

"heteroloweralkylidenyl" refers to a loweralkylidenyl hydrocarbon group containing from about 2 to 5 carbon atoms and having one or more hetero atoms in the chain selected from O, N or S, such as piperidinyl, morpholinyl, etc.

Representative heteryl rings include such as thienyl, furyl, pyridyl, pyrazinyl, pyrimidinyl, pyridazinyl, triazinyl isoxazolyl, isothiazolyl, pyrrolyl, imidazolyl, pyrazolyl, pyranyl, 2H-pyrrolyl, imidazolidinyl, imidazolinyl, pyrazolidinyl, pyrrolidinyl, pyrrolinyl, piperidyl, piperazinyl and morpholinyl.

Representative compounds of this invention which are particularly useful include:
α-phenyl-N-phenylnitrone α-hydroxyphenyl-N-phenylnitrone
α-phenyl-N-hydroxyphenylnitrone
α-hydroxyphenyl-N-hydroxyphenylnitrone
α-halophenyl-N-phenylnitrone
α-phenyl-N-halophenylnitrone
α-halophenyl-N-halophenylnitrone
α-hydroxyphenyl-N-halophenylnitrone
αhalophenyl-N-hydroxyphenylnitrone
α-phenyl-N-alkylphenylnitrone
α-alkylphenyl-N-phenylnitrone
α-alkylphenyl-N-alkylphenylnitrone
α-halophenyl-N-alkylphenylnitrone
α-alkylphenyl-N-halophenylnitrone
α-alkylphenyl-N-hydroxyphenylnitrone
α-loweralkylhalophenyl-N-phenylnitrone
α-loweralkylhalophenyl-N-halophenylnitrone
α-loweralkylhalophenyl-N-hydroxyphenylnitrone
α-phenyl-N-loweralkylhalophenylnitrone
α-halophenyl-N-loweralkylhalophenylnitrone
α-hydroxyphenyl-N-loweralkylhalophenylnitrone
α-halohydroxyphenyl-N-phenylnitrone
α-alkylhydroxyphenyl-N-phenylnitrone
α-alkylhalophenyl-N-phenylnitrone
α-phenyl-N-halohydroxyphenylnitrone
α-phenyl-N-alkylhydroxyphenylnitrone
α-phenyl-N-alkylhalophenylnitrone
α-phenyl-N-alkoxyphenylnitrone
α-alkoxyphenyl-N-phenylnitrone
α-halophenyl-N-alkoxyphenylnitrone
α-alkoxyphenyl-N-halophenylnitrone
α-p-biphenyl-N-phenylnitrone
α-p-biphenyl-N-halophenylnitrone
α-phenyl-N-p-biphenylnitrone
α-alkylphenyl-N-p-cyclohexylphenylnitrone
α-alkylphenyl-N-p-morpholinylphenylnitrone
α-alkylphenyl-N-p-thienylphenylnitrone
α-p-cyclohexylphenyl-N-hydroxyphenylnitrone
α-p-morpholinylphenyl-N-hydroxyphenylnitrone
α-p-thienylphenyl-N-hydroxyphenylnitrone
α-sulfinylphenyl-N-hydroxyphenylnitrone
α-loweralkylhalophenyl-N-p-cyclohexylphenylnitrone
α-halophenyl-N-p-cyclohexylphenylnitrone
α-hydroxyphenyl-N-p-cyclohexylphenylnitrone
α-p-cyclohexylphenyl-N-loweralkylhalophenylnitrone
α-halophenyl-N-cyclohexylphenylnitrone
α-hydroxyphenyl-N-cyclohexylphenylnitrone
α-halohydroxyphenyl-N-p-cyclohexylphenylnitrone
α-alkylhydroxyphenyl-N-p-cyclohexylphenylnitrone
α-alkylhalophenyl-N-p-cyclohexylphenylnitrone
α-p-biphenyl-N-halohydroxyphenylnitrone
α-p-biphenyl-N-alkylhydroxyphenylnitrone
α-p-biphenyl-N-alkylhalophenylnitrone The compounds of this invention may be prepared by the following general procedures.

Condensation of a phenylhydroxyamine with a benzaldehyde compound in 95% ethanol.

The following reaction equation illustrates this synthesis:

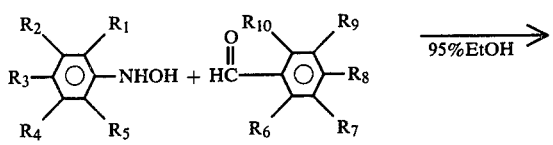

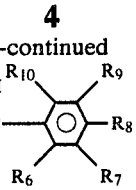 (I)

where $R_1$, $R_2$, $R_3$, $R_4$, $R_5$, $R_6$, $R_7$, $R_8$, $R_9$ and $R_{10}$ are as described above.

An alternate method for the production of compounds of Formula I involves utilizing an exchange reaction of phenylhydroxylamines with anils by the following general procedure:

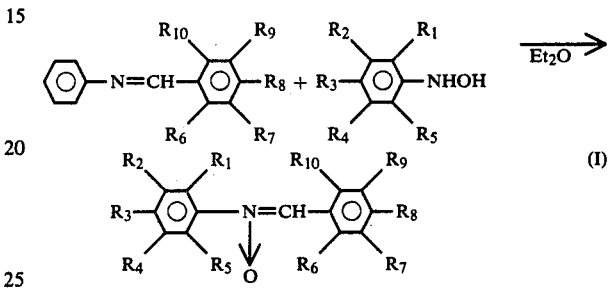

In this reaction, the aniline moiety of the anil is replaced by the substituted aniline moiety of the hydroxylamine.

The intermediate compounds of this invention according to this procedure may be prepared by the following general procedures.

Condensation of aniline with a substituted benzaldehyde along the procedures as described by Gillman and Blatt, Organic Synthesis, Coll. Vol. I, 2nd Ed. N. Y. John Wiley and Sons, pages 80–81 results in the desired anil which can then be reacted as above with the desired phenylhydroxyamine.

The following reaction equation illustrates this synthesis:

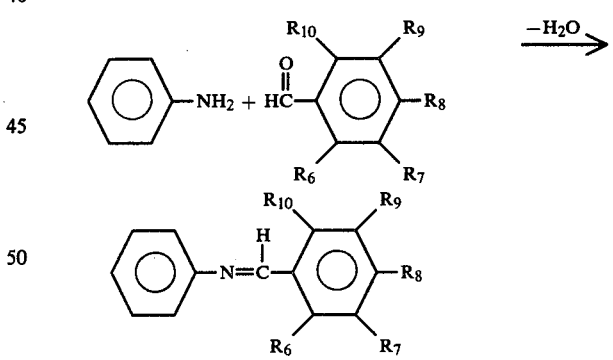

where $R_1$, $R_2$, $R_3$, $R_4$, $R_5$, $R_6$, $R_7$, $R_8$, $R_9$ and $R_{10}$ are as described above.

An alternate method for the production of certain intermediate compounds involves the distillation of a product from a neat mixture of a benzaldehyde compound and an aniline derivative at an elevated temperature and under a reduced pressure. This gives the desired anil as above.

Preparation of the desired phenylhydroxylamine can be carried out in the customary manner by reduction of the corresponding nitrophenyl or nitrosophenyl compound with zinc dust and ammonium chloride in an ethanol media. When this is also carried out in the presence of a suitable benzaldehyde, then the desired nitrone product may be obtained directly.

In accordance with the present invention, a method of treating inflammation in warmblooded animals is provided which comprises topically administering to the subject in need of such treatment an effective amount of a compound of Formula I.

As used herein, the term "treatment" is meant to include both active treatment and preventative or prophylactic treatment.

The present invention also has for its object compositions for treating conditions requiring anti-inflammatory treatment containing at least one of the compounds of Formula I in an amount of about 0.05–5.0% by weight of the composition, preferably from about 0.1–1.0% by weight. These compositions can be in the form of a solution, a cream, a powder, gel, ointment, salve, lotion or milk. They can also constitute makeup products or dermatological cakes containing the ingredients standard to these types of compositions.

The following Examples will further illustrate the formulations containing the compounds of Formula I but are not to be considered as limiting the scope of this invention.

Preparation of Intermediates

EXAMPLE A

N-Benzylideneaniline

Benzaldehyde (0.20 mole) was treated with aniline (0.20 mole) with vigorous stirring in a 1 l. Erlenmeyer Flask. After 15 mins., 33 cc of 95% ethanol was added and the reaction mixture was stirred vigorously for an additional 5 minutes. The reaction mixture was left standing at room temperature for 10 min.; then it was placed in an ice-bath for 0.5 hrs. The crystals which formed were collected, washed with 95% ethanol, and air-dried. Recrystallization from 85% ethanol gave 21.5 g. of N-benzylideneaniline product. m.p. 50°–51.5°.

EXAMPLE B

When the above reaction is carried out and the benzaldehyde is replaced with an equimolar amount of a substituted benzaldehyde of Table I, below, then the corresponding anil compound of Table II, below, is prepared.

Table I o-hydroxybenzaldehyde
m-hydroxybenzaldehyde
p-hydroxybenzaldehyde
2,3-dihydroxybenzaldehyde
2,4-dihydroxybenzaldehyde
2,5-dihydroxybenzaldehyde
2,6-dihydroxybenzaldehyde
3,4-dihydroxybenzaldehyde
3,5-dihydroxybenzaldehyde
2,3,4-trihydroxybenzaldehyde
2,4,6-trihydroxybenzaldehyde
3,4,5-trihydroxybenzaldehyde
p-phenylbenzaldehyde
o-chlorobenzaldehyde
m-chlorobenzaldehyde
p-chlorobenzaldehyde
2,3-dichlorobenzaldehyde
2,4-dichlorobenzaldehyde
2,5-dichlorobenzaldehyde
2,6-dichlorobenzaldehyde
3,4-dichlorobenzaldehyde
3,5-dichlorobenzaldehyde
2,3,4-trichlorobenzaldehyde
2,4,6-trichlorobenzaldehyde
o-fluorobenzaldehyde
m-fluorobenzaldehyde
p-fluorobenzaldehyde
p-bromobenzaldehyde
2,3-difluorobenzaldehyde
2,4-difluorobenzaldehyde
2,5-difluorobenzaldehyde
2,6-difluorobenzaldehyde
3,4-difluorobenzaldehyde
3,5-difluorobenzaldehyde
2,3,4-trifluorobenzaldehyde
2,4,6-trifluorobenzaldehyde
5-methylbenzaldehyde
m-methylbenzaldehyde
p-methylbenzaldehyde
o-ethylbenzaldehyde
p-ethylbenzaldehyde
m-bromobenzaldehyde
p-bromobenzaldehyde
3-chloro-4-cyclohexylbenzaldehyde
2-chloro-3-methylbenzaldehyde
2-chloro-4-methylbenzaldehyde
2-chloro-5-methylbenzaldehyde
2-chloro-6-methylbenzaldehyde
2-methyl-3-chlorobenzaldehyde
2-methyl-4-chlorobenzaldehyde
2-methyl-3-fluorobenzaldehyde
2-methyl-4-fluorobenzaldehyde
2-methyl-5-fluorobenzaldehyde
2-methyl-6-fluorobenzaldehyde
2-fluoro-3-methylbenzaldehyde
2-fluoro-4-methylbenzaldehyde
2-fluoro-5-methylbenzaldehyde
o-trifluoromethylbenzaldehyde
m-trifluoromethylbenzaldehyde
p-trifluoromethylbenzaldehyde
2-methyl-3-trifluoromethylbenzaldehyde
2-methyl-4-trifluoromethylbenzaldehyde
2-methyl-5-trifluoromethylbenzaldehyde
3-methyl-2-trifluoromethylbenzaldehyde
2-chloro-3-trifluoromethylbenzaldehyde
2-chloro-4-trifluoromethylbenzaldehyde
3-chloro-2-trifluoromethylbenzaldehyde
3-chloro-4-trifluoromethylbenzaldehyde
p-phenylbenzaldehyde
p-cyclohexylbenzaldehyde
p-trifluoromethoxybenzaldehyde
o-methoxybenzaldehyde
m-methoxybenzaldehyde
p-methoxybenzaldehyde Table II o-hydroxybenzylideneaniline
m-hydroxybenzylideneaniline
p-hydroxybenzylideneaniline
2,3-dihydroxybenzylideneaniline
2,4-dihydroxybenzylideneaniline
2,5-dihydroxybenzylideneaniline
2,6-dihydroxybenzylideneaniline
3,4-dihydroxybenzylideneaniline
3,5-dihydroxybenzylideneaniline
2,3,4-trihydroxybenzylideneaniline
2,4,6-trihydroxybenzylideneaniline
3,4,5-trihydroxybenzylideneaniline p-phenylbenzylideneaniline
o-chlorobenzylideneaniline
m-chlorobenzylideneaniline
p-chlorobenzylideneaniline
2,3-dichlorobenzylideneaniline
2,4-dichlorobenzylideneaniline
2,5-dichlorobenzylideneaniline
2,6-dichlorobenzylideneaniline
3,4-dichlorobenzylideneaniline
3,5-dichlorobenzylideneaniline
2,3,4-trichlorobenzylideneaniline
2,4,6-trichlorobenzylideneaniline
o-fluorobenzylideneaniline
m-fluorobenzylideneaniline
p-fluorobenzylideneaniline
p-bromobenzylideneaniline
2,3-difluorobenzylideneaniline
2,4-difluorobenzylideneaniline
2,5-difluorobenzylideneaniline
2,6-difluorobenzylideneaniline
3,4-difluorobenzylideneaniline
3,5-difluorobenzylideneaniline
2,3,4-trifluorobenzylideneaniline
2,4,6-trifluorobenzylideneaniline
5-methylbenzylideneaniline
m-methylbenzylideneaniline
p-methylbenzylideneaniline
o-ethylbenzylideneaniline
p-ethylbenzylideneaniline
m-bromobenzylideneaniline
p-bromobenzylideneaniline
3-chloro-4-cyclohexylbenzylideneaniline
2-chloro-3-methylbenzylideneaniline
2-chloro-4-methylbenzylideneaniline
2-chloro-5-methylbenzylideneaniline
2-chloro-6-methylbenzylideneaniline
2-methyl-3-chlorobenzylideneaniline
2-methyl-4-chlorobenzylideneaniline
2-methyl-3-fluorobenzylideneaniline
2-methyl-4-fluorobenzylideneaniline
2-methyl-5-fluorobenzylideneaniline
2-methyl-6-fluorobenzylideneaniline
2-fluoro-3-methylbenzylideneaniline
2-fluoro-4-methylbenzylideneaniline
2-fluoro-5-methylbenzylideneaniline
o-trifluoromethylbenzylideneaniline
m-trifluoromethylbenzylideneaniline
p-trifluoromethylbenzylideneaniline
2-methyl-3-trifluoromethylbenzylideneaniline
2-methyl-4-trifluoromethylbenzylideneaniline
2-methyl-5-trifluoromethylbenzylideneaniline
3-methyl-2-trifluoromethylbenzylideneaniline
2-chloro-3-trifluoromethylbenzylideneaniline
2-chloro-4-trifluoromethylbenzylideneaniline
3-chloro-2-trifluoromethylbenzylideneaniline
3-chloro-4-trifluoromethylbenzylideneaniline
p-phenylbenzylideneaniline
p-cyclohexylideneaniline
p-trifluoromethoxybenzylideneaniline
o-methoxybenzylideneaniline
m-methoxybenzylideneaniline
p-methoxybenzylideneaniline

EXAMPLE C

N-Phenylhydroxylamine

To a well stirred mixture of nitrobenzene (12.3 g.; 0.10 mole) and ammonium chloride (6.1 g. in 100 ml. H₂O) in 100 ml. of ethanol was added zinc dust (13.1 g.) over a 15 minute period. The reaction mixture was exothermic. After addition of the zinc had been completed, the reaction mixture was allowed to stir for 15 mins.; it was then filtered and the filter cake was washed with hot ethanol. The filtrate was concentrated and the residue extracted into ether which was then washed with saline and dried over sodium sulfate. Removal of the solvent and trituration of the residue with petrolatum ether gave N-phenylhydroxylamine.

EXAMPLE D

When the above reaction of Example C is carried out and the nitrobenzene is replaced with an equimolar amount of a substituted nitrobenzene of Table III, below, then the corresponding phenylhydroxylamine compound is prepared.

Table III o-chloronitrobenzene
m-chloronitrobenzene
p-chloronitrobenzene
2,3-dichloronitrobenzene
2,4-dichloronitrobenzene
2,5-dichloronitrobenzene
2,6-dichloronitrobenzene
3,4-dichloronitrobenzene
3,5-dichloronitrobenzene
o-fluoronitrobenzene
m-fluoronitrobenzene
p-fluoronitrobenzene
o-trifluoromethylnitrobenzene
m-trifluoromethylnitrobenzene
p-trifluoromethylnitrobenzene
p-bromonitrobenzene
o-methylnitrobenzene
m-methylnitrobenzene
p-methylnitrobenzene
o-ethylnitrobenzene
m-ethylnitrobenzene
p-ethylnitrobenzene
p-phenylnitrobenzene
p-cyclohexylnitrobenzene
p-trifluoromethoxynitrobenzene
o-methoxynitrobenzene
m-methoxynitrobenzene
p-methoxynitrobenzene
p-acetylnitrobenzene
p-mercaptonitrobenzene
p-cyanonitrobenzene
2-chloro-3-methylnitrobenzene
2-chloro-4-methylnitrobenzene
2-chloro-5-methylnitrobenzene
2-chloro-6-methylnitrobenzene
3-chloro-2-methylnitrobenzene
3-chloro-4-methylnitrobenzene
2-chloro-3-trifluoromethylnitrobenzene
2-chloro-4-trifluoromethylnitrobenzene
3-chloro-2-trifluoromethylnitrobenzene
3-chloro-4-trifluoromethylnitrobenzene
2-chloro-4-fluoronitrobenzene
2-trifluoromethyl-3-chloronitrobenzene
2-trifluoromethyl-4-chloronitrobenzene
3-trifluoromethyl-2-chloronitrobenzene
3-trifluoromethyl-4-chloronitrobenzene
2-trifluoromethyl-3-fluoronitrobenzene
2-trifluoromethyl-4-fluoronitrobenzene
3-trifluoromethyl-2-fluoronitrobenzene 3-trifluoromethyl-4-fluoronitrobenzene
2-fluoro-3-methylnitrobenzene
2-fluoro-4-methylnitrobenzene
2-fluoro-5-methylnitrobenzene
2-fluoro-6-methylnitrobenzene
3-fluoro-2-methylnitrobenzene
3-fluoro-4-methylnitrobenzene
2-fluoro-3-trifluoromethylnitrobenzene
2-fluoro-4-trifluoromethylnitrobenzene
3-fluoro-2-trifluoromethylnitrobenzene
3-fluoro-4-trifluoromethylnitrobenzene
2-fluoro-4-chloronitrobenzene
o-hydroxynitrobenzene
m-hydroxynitrobenzene
p-hydroxynitrobenzene
3,4-dihydroxynitrobenzene
3,4,5-trihydroxynitrobenzene
2-hydroxy-3-methylnitrobenzene
2-hydroxy-4-methylnitrobenzene
2-hydroxy-3-chloronitrobenzene
2-hydroxy-4-chloronitrobenzene
2-hydroxy-3-fluoronitrobenzene
2-hydroxy-4-fluoronitrobenzene
3-hydroxy-2-methylnitrobenzene
3-hydroxy-2-chloronitrobenzene
3-hydroxy-2-fluoronitrobenzene
2-methoxy-3-chloronitrobenzene
2-methoxy-4-chloronitrobenzene
3-methoxy-2-chloronitrobenzene
2-methoxy-4-fluoronitrobenzene
2-methoxy-3-methylnitrobenzene
2-methoxy-4-methylnitrobenzene
3-methoxy-2-methylnitrobenzene
3-chloro-4-cyclohexylnitrobenzene
2-methyl-4-chloronitrobenzene
2-methyl-4-fluoronitrobenzene
2-methyl-4-methoxynitrobenzene
2-methyl-4-trifluoromethylnitrobenzene
2,3-dimethylnitrobenzene
2,4-dimethylnitrobenzene
2,5-dimethylnitrobenzene
2,6-dimethylnitrobenzene
3,4-dimethylnitrobenzene
3,5-dimethylnitrobenzene

TABLE IV o-chlorophenylhydroxylamine
m-chlorophenylhydroxylamine
p-chlorophenylhydroxylamine
2,3-dichlorophenylhydroxylamine
2,4-dichlorophenylhydroxylamine
2,5-dichlorophenylhydroxylamine
2,6-dichlorophenylhydroxylamine
3,4-dichlorophenylhydroxylamine
3,5-dichlorophenylhydroxylamine
o-fluorophenylhydroxylamine
m-fluorophenylhydroxylamine
p-fluorophenylhydroxylamine
o-trifluoromethylphenylhydroxylamine
m-trifluoromethylphenylhydroxylamine
p-trifluoromethylphenylhydroxylamine
p-bromophenylhydroxylamine
o-methylphenylhydroxylamine
m-methylphenylhydroxylamine
p-methylphenylhydroxylamine
o-ethylphenylhydroxylamine
m-ethylphenylhydroxylamine
p-ethylphenylhydroxylamine
p-biphenylhydroxylamine
p-cyclohexylphenylhydroxylamine
p-trifluoromethoxyphenylhydroxylamine
o-methoxyphenylhydroxylamine
m-methoxyphenylhydroxylamine
p-methoxyphenylhydroxylamine
p-acetylphenylhydroxylamine
p-mercaptophenylhydroxylamine
p-cyanophenylhydroxylamine
2-chloro-3-methylphenylhydroxylamine
2-chloro-4-methylphenylhydroxylamine
2-chloro-5-methylphenylhydroxylamine
2-chloro-6-methylphenylhydroxylamine
3-chloro-2-methylphenylhydroxylamine
3-chloro-4-methylphenylhydroxylamine
2-chloro-3-trifluoromethylhydroxylamine
2-chloro-4-trifluoromethylphenylhydroxylamine
3-chloro-2-trifluoromethylphenylhydroxylamine
3-chloro-4-trifluoromethylphenylhydroxylamine
2-chloro-4-fluorophenylhydroxylamine
2-trifluoromethyl-3-chlorophenylhydroxylamine
2-trifluoromethyl-4-chlorophenylhydroxylamine
3-trifluoromethyl-2-chlorophenylhydroxylamine
3-trifluoromethyl-4-chlorophenylhydroxylamine
2-trifluoromethyl-3-fluorophenylhydroxylamine
2-trifluoromethyl-4-fluorophenylhydroxylamine
3-trifluoromethyl-2-fluorophenylhydroxylamine
3-trifluoromethyl-4-fluorophenylhydroxylamine
2-fluoro-3-methylphenylhydroxylamine
2-fluor-4-methylphenylhydroxylamine
2-fluoro-4-methylphenylhydroxylamine
2-fluoro-5-methylphenylhydroxylamine
2-fluoro-6-methylphenylhydroxylamine
3-fluoro-2-methylphenylhydroxylamine
3-fluoro-4-methylphenylhydroxylamine
2-fluoro-3-trifluoromethylphenylhydroxylamine
2-fluoro-4-trifluoromethylphenylhydroxylamine
3-fluoro-2-trifluoromethylphenylhydroxylamine
3-fluoro-4-trifluoromethylphenylhydroxylamine
2-fluoro-4-chlorophenylhydroxylamine
o-hydroxylphenylhydroxylamine
m-hydroxylphenylhydroxylamine
p-hydroxylphenylhydroxylamine
3,4-dihydroxyphenylhydroxylamine
3,4,5-trihydroxyphenylhydroxylamine
2-hydroxy-3-methylphenylhydroxylamine
2-hydroxy-4-methylphenylhydroxylamine
2-hydroxy-3-chlorophenylhydroxylamine
2-hydroxy-4-chlorophenylhydroxylamine
2-hydroxy-3-fluorophenylhydroxylamine
2-hydroxy-4-fluorophenylhydroxylamine
3-hydroxy-2-methylphenylhydroxylamine
3-hydroxy-2-chlorophenylhydroxylamine
3-hydroxy-2-fluorophenylhydroxylamine
2-methoxy-3-chlorophenylhydroxylamine
2-methoxy-4-chlorophenylhydroxylamine
3-methoxy-2-chlorophenylhydroxylamine
2-methoxy-4-fluorophenylhydroxylamine
2-methoxy-3-methylphenylhydroxylamine
2-methoxy-4-methylphenylhydroxylamine
3-methoxy-2-methylphenylhydroxylamine
3-chloro-4-cyclohexylphenylhydroxylamine
2-methyl-4-chlorophenylhydroxylamine
2-methyl-4-fluorophenylhydroxylamine
2-methyl-4-methoxyphenylhydroxylamine
2-methyl-4-trifluoromethylphenylhydroxylamine
2,3-dimethylphenylhydroxylamine
2,4-dimethylphenylhydroxylamine 2,5-dimethylphenylhydroxylamine
2,6-dimethylphenylhydroxylamine
3,4-dimethylphenylhydroxylamine
3,5-dimethylphenylhydroxylamine Preparation of Active Compounds

EXAMPLE 1

α-Phenyl-N-p-chlorophenylnitrone p-Chlorophenylhydroxylamine (0.05 moles) was dissolved in warm 95% ethanol (20 cc) and was treated with benzaldehyde (0.05 moles) with vigorous stirring. The solid which formed was collected, washed with 95% ethanol, and recrystallized from ethanol to give 512 g. of α-phenyl-N-p-chlorophenylnitrone (m.p. 179°–182°).

EXAMPLE 2

α-Phenyl-N-2-chlorophenylnitrone o-Chlorophenylhydroxylamine (0.05 moles) was dissolved in warm 95% ethanol (20 cc) and was treated with benzaldehyde (0.05 moles) with vigorous stirring. The solid which formed was from ethanol to give α-phenyl-N-2-chlorophenylnitrone.

EXAMPLE 3

α-p-Bromophenyl-N-p-chlorophenylnitrone p-Chlorophenylhydroxylamine (0.05 moles) was dissolved in warm 95% ethanol (20 cc) and was treated with p-bromobenzaldehyde (0.05 moles) with vigorous stirring. The solid which formed was collected, washed with 95% ethanol, and was recrystallized from ethanol to give α-p-bromophenyl-N-p-chlorophenylnitrone.

EXAMPLE 4

α-2,4-Dibromophenyl-N-p-methoxyphenylnitrone p-Methoxyphenylhydroxylamine (0.05 moles) was dissolved in warm 95% ethanol (20 cc) with vigorous stirring. The solid which formed was collected, washed with 95% ethanol, and was recrystallized from ethanol to give α-2,4-dibromophenyl-N-p-methoxyphenylnitrone.

EXAMPLE 5

α-p-Cyclohexylphenyl-N-p-chlorophenylnitrone p-Chlorophenylhydroxylamine (0.05 moles) was dissolved in warm 95% ethanol (40 cc) and was treated with p-cyclohexylbenzaldehyde (0.05 moles) with vigorous stirring. The solid which formed was collected, washed with 95% ethanol, and was recrystallized from ethanol to give α-p-cyclohexylphenyl-N-p-chlorophenylnitrone.

EXAMPLE 6

α-p-Chlorophenyl-N-phenylnitrone

N-phenylhydroxylamine (0.052 mole) was dissolved in ether (20 cc). This solution was treated with N-(p-chlorobenzylidene)-2-methyl-4-chloroaniline (13.8 g.) dissolved in ether (50 cc). After 15 min., white crystals had begun to form. Filtration and washing with ether gave α-p-chlorophenyl-N-phenylnitrone.

EXAMPLE 7

α-p-Chlorophenyl-N-p-fluorophenylnitrone

N-p-fluorophenylhydroxylamine (0.052 moles) was dissolved in ether (20 cc). This solution was treated with N-p-chlorobenzylideneaniline (0.05 moles) and dissolved in ether (50 cc). The product which separated was filtered and washed with ether to give α-p-chlorophenyl-N-p-fluorophenylnitrone.

EXAMPLE 8

Following the process of Example 7 but substituting N-p-chlorobenzylideneaniline with any of the compounds obtained by Examples A & B, there is obtained the corresponding α-phenyl-N-phenylnitrone compound.

EXAMPLE 9

When the procedure of Example 7 is followed and the N-p-fluorophenylhydroxylamine is replaced by any of the hydroxylamine compounds of Examples C and D, then the corresponding α-phenyl-N-phenylnitrone product is obtained.

EXAMPLE 10

When the foregoing examples are followed and the corresponding intermediate materials are used, then the desired nitrone products are obtained. A representative list of nitrone products so obtained is shown in Table V below.

Table V

α-phenyl-N-phenylnitrone
α-o-chlorophenyl-N-phenylnitrone
α-m-chlorophenyl-N-phenylnitrone
α-p-chlorophenyl-N-phenylnitrone
α-(2,3-dichlorophenyl)-N-phenylnitrone
α-(2,4-dichlorophenyl)-N-phenylnitrone
α-(2,5-dichlorophenyl)-N-phenylnitrone
α-(2,6-dichlorophenyl)-N-phenylnitrone
α-(3,4-dichlorophenyl)-N-phenylnitrone
α-(3,5-dichlorophenyl)-N-phenylnitrone
α-(2,3,4-trichlorophenyl)-N-phenylnitrone
α-(2,3,5-trichlorophenyl)-N-phenylnitrone
α-(2,3,6-trichlorophenyl)-N-phenylnitrone
α-(2,4,5-trichlorophenyl)-N-phenylnitrone
α-(2,4,6-trichlorophenyl)-N-phenylnitrone
α-(3,4,5-trichlorophenyl)-N-phenylnitrone
α-o-fluorophenyl-N-phenylnitrone
α-m-fluorophenyl-N-phenylnitrone
α-p-fluorophenyl-N-phenylnitrone
α-(2,3-difluorophenyl)-N-phenylnitrone
α-(2,4-difluorophenyl)-N-phenylnitrone
α-(2,5-difluorophenyl)-N-phenylnitrone
α-(2,6-difluorophenyl)-N-phenylnitrone
α-p-bromophenyl-N-phenylnitrone
α-o-trifluoromethylphenyl-N-phenylnitrone
α-m-trifluoromethylphenyl-N-phenylnitrone
α-p-trifluoromethylphenyl-N-phenylnitrone
α-o-methylphenyl-N-phenylnitrone
α-m-methylphenyl-N-phenylnitrone
α-p-methylphenyl-N-phenylnitrone
α-(2,3-dimethylphenyl)-N-phenylnitrone
α-(2,4-dimethylphenyl)-N-phenylnitrone
α-(2,5-dimethylphenyl)-N-phenylnitrone
α-(2,6-dimethylphenyl)-N-phenylnitrone
α-(3,4-dimethylphenyl)-N-phenylnitrone
α-(3,5-dimethylphenyl)-N-phenylnitrone
α-(2,3,4-trimethylphenyl)-N-phenylnitrone
α-(2,3,5-trimethylphenyl)-N-phenylnitrone
α-(2,3,6-trimethylphenyl)-N-phenylnitrone
α-(2,4,5-trimethylphenyl)-N-phenylnitrone α-(2,4,6-trimethylphenyl)-N-phenylnitrone
α-(3,4,5-trimethylphenyl)-N-phenylnitrone
α-o-ethylphenyl-N-phenylnitrone
α-m-ethylphenyl-N-phenylnitrone
α-p-ethylphenyl-N-phenylnitrone
α-(2-methyl-4-ethylphenyl)-N-phenylnitrone
α-(2-ethyl-4-methylphenyl)-N-phenylnitrone
α-(2-methyl-6-ethylphenyl)-N-phenylnitrone
α-o-methoxyphenyl-N-phenylnitrone
α-m-methoxyphenyl-N-phenylnitrone
α-p-methoxyphenyl-N-phenylnitrone
α-(2,4-dimethoxyphenyl)-N-phenylnitrone
α-(3,4-dimethoxyphenyl)-N-phenylnitrone
α-p-ethoxyphenyl-N-phenylnitrone
α-o-hydroxyphenyl-N-phenylnitrone
α-m-hydroxyphenyl-N-phenylnitrone
α-p-hydroxyphenyl-N-phenylnitrone
α-(2,3-dihydroxyphenyl)-N-phenylnitrone
α-(2,4-dihydroxyphenyl)-N-phenylnitrone
α-(3,4-dihydroxyphenyl)-N-phenylnitrone
α-(3,4,5-trihydroxyphenyl)-N-phenylnitrone
α-p-trifluoromethoxyphenyl-N-phenylnitrone
α-p-acetylphenyl-N-phenylnitrone
α-p-acetyloxyphenyl-N-phenylnitrone
α-p-mercaptophenyl-N-phenylnitrone
α-p-acetylthiophenyl-N-phenylnitrone
α-p-methylthiophenyl-N-phenylnitrone
α-p-methylsulfinylphenyl-N-phenylnitrone
α-p-methylsulfonylphenyl-N-phenylnitrone
α-p-nitrophenyl-N-phenylnitrone
α-p-aminophenyl-N-phenylnitrone
α-p-cyclohexylphenyl-N-phenylnitrone
α-[p-(2-cyclohexenylphenyl)]-N-phenylnitrone
α-p-biphenyl-N-phenylnitrone
α-[p-(2-thienylphenyl)]-N-phenylnitrone
α-[p-(2-morpholinylphenyl)]-N-phenylnitrone
α-(2-methyl-3-chlorophenyl)-N-phenylnitrone
α-(2-methyl-4-chlorophenyl)-N-phenylnitrone
α-(2-methyl-5-chlorophenyl)-N-phenylnitrone
α-(2-methyl-6-chlorophenyl)-N-phenylnitrone
α-(3-methyl-2-chlorophenyl)-N-phenylnitrone
α-(3-methyl-4-chlorophenyl)-N-phenylnitrone
α-(2-ethyl-4-chlorophenyl)-N-phenylnitrone
α-(2-methyl-3-fluorophenyl)-N-phenylnitrone
α-(2-methyl-4-fluorophenyl)-N-phenylnitrone
α-(2-methyl-5-fluorophenyl)-N-phenylnitrone
α-(2-methyl-6-fluorophenyl)-N-phenylnitrone
α-(3-methyl-2-fluorophenyl)-N-phenylnitrone
α-(3-methyl-4-fluorophenyl)-N-phenylnitrone
α-(2-methyl-4-bromophenyl)-N-phenylnitrone
α-(2-methyl-4-trifluoromethylphenyl)-N-phenylnitrone
α-(2-methyl-4-methoxyphenyl)-N-phenylnitrone
α-(2-methyl-4-hydroxyphenyl)-N-phenylnitrone
α-(2-methyl-4-nitrophenyl)-N-phenylnitrone
α-(2-methyl-4-ethylphenyl)-N-phenylnitrone
α-(4-methyl-2-chlorophenyl)-N-phenylnitrone
α-(4-methyl-3-chlorophenyl)-N-phenylnitrone
α-(4-methyl-2-fluorophenyl)-N-phenylnitrone
α-(4-methyl-3-fluorophenyl)-N-phenylnitrone
α-(4-methyl-2-trifluoromethylphenyl)-N-phenylnitrone
α-(4-methyl-3-trifluoromethylphenyl)-N-phenylnitrone
α-(4-methyl-2-hydroxyphenyl)-N-phenylnitrone
α-(4-methyl-3-hydroxyphenyl)-N-phenylnitrone
α-(4-methyl-2-ethylphenyl)-N-phenylnitrone
α-(2-chloro-4-bromophenyl)-N-phenylnitrone
α-(2-chloro-4-fluorophenyl)-N-phenylnitrone
α-(2-chloro-4-hydroxyphenyl)-N-phenylnitrone
α-(2-chloro-4-methoxyphenyl)-N-phenylnitrone
α-(2-chloro-4-nitrophenyl)-N-phenylnitrone
α-(2-chloro-4-trifluoromethylphenyl)-N-phenylnitrone
α-(2-chloro-4-ethylphenyl)-N-phenylnitrone
α-(2-fluoro-5-methylphenyl)-N-phenylnitrone
α-(2-fluoro-4-bromophenyl)-N-phenylnitrone
α-(2-fluoro-4-hydroxyphenyl)-N-phenylnitrone
α-(2-fluoro-4-methoxyphenyl)-N-phenylnitrone
α-(2-fluoro-4-nitrophenyl)-N-phenylnitrone
α-(2-fluoro-4-trifluoromethylphenyl)-N-phenylnitrone
α-(2-fluoro-4-ethylphenyl)-N-phenylnitrone
α-(2-hydroxy-4-nitrophenyl)-N-phenylnitrone
α-(2-hydroxy-4-trifluoromethylphenyl)-N-phenylnitrone
α-phenyl-N-o-chlorophenylnitrone
α-phenyl-N-m-chlorophenylnitrone
α-phenyl-N-p-chlorophenylnitrone
α-phenyl-N-(2,3-dichlorophenyl)nitrone
α-phenyl-N-(2,4-dichlorophenyl)nitrone
α-phenyl-N-(2,5-dichlorophenyl)nitrone
α-phenyl-N-(2,6-dichlorophenyl)nitrone
α-phenyl-N-(3,4-dichlorophenyl)nitrone
α-phenyl-N-(3,5-dichlorophenyl)nitrone
α-phenyl-N-(2,3,4-trichlorophenyl)nitrone
α-phenyl-N-(2,3,5-trichlorophenyl)nitrone
α-phenyl-N-(2,3,6-trichlorophenyl)nitrone
α-phenyl-N-(2,4,5-trichlorophenyl)nitrone
α-phenyl-N-(2,4,6-trichlorophenyl)nitrone
α-phenyl-N-(3,4,5-trichlorophenyl)nitrone
α-phenyl-N-o-fluorophenylnitrone
α-phenyl-N-m-fluorophenylnitrone
α-phenyl-N-p-fluorophenylnitrone
α-phenyl-N-(2,3-difluorophenyl)nitrone
α-phenyl-N-(2,4-difluorophenyl)nitrone
α-phenyl-N-(2,5-difluorophenyl)nitrone
α-phenyl-N-(2,6-difluorophenyl)nitrone
α-phenyl-N-p-bromophenylnitrone
α-phenyl-N-o-trifluoromethylphenylnitrone
α-phenyl-N-m-trifluoromethylphenylnitrone
α-phenyl-N-p-trifluoromethylphenylnitrone
α-phenyl-N-o-methylphenylnitrone
α-phenyl-N-m-methylphenylnitrone
α-phenyl-N-p-methylphenylnitrone
α-phenyl-N-(2,3-dimethylphenyl)nitrone
α-phenyl-N-(2,4-dimethylphenyl)nitrone
α-phenyl-N-(2,5-dimethylphenyl)nitrone
α-phenyl-N-(2,6-dimethylphenyl)nitrone
α-phenyl-N-(3,4-dimethylphenyl)nitrone
α-phenyl-N-(3,5-dimethylphenyl)nitrone
α-phenyl-N-(2,3,4-trimethylphenyl)nitrone
α-phenyl-N-(2,3,5-trimethylphenyl)nitrone
α-phenyl-N-(2,3,6-trimethylphenyl)nitrone
α-phenyl-N-(2,4,5-trimethylphenyl)nitrone
α-phenyl-N-(2,4,6-trimethylphenyl)nitrone
α-phenyl-N-(3,4,5-trimethylphenyl)nitrone
α-phenyl-N-o-ethylphenylnitrone
α-phenyl-N-m-ethylphenylnitrone
α-phenyl-N-p-ethylphenylnitrone
α-phenyl-N-(2-methyl-4-ethylphenyl)nitrone
α-phenyl-N-(2-ethyl-4-methylphenyl)nitrone
α-phenyl-N-(2-methyl-6-ethylphenyl)nitrone
α-phenyl-N-o-methoxyphenylnitrone
α-phenyl-N-m-methoxyphenylnitrone
α-phenyl-N-p-methoxyphenylnitrone α-phenyl-N-(2,4-dimethoxyphenyl)nitrone
α-phenyl-N-(3,4-dimethoxyphenyl)nitrone
α-phenyl-N-p-ethoxyphenylnitrone
α-phenyl-N-o-hydroxyphenylnitrone
α-phenyl-N-m-hydroxyphenylnitrone
α-phenyl-N-p-hydroxyphenylnitrone
α-phenyl-N-(2,3-dihydroxyphenyl)nitrone
α-phenyl-N-(2,4-dihydroxyphenyl)nitrone
α-phenyl-N-(3,4-dihydroxyphenyl)nitrone
α-phenyl-N-(3,4,5-trihydroxyphenyl)nitrone
α-phenyl-N-p-trifluoromethoxyphenylnitrone
α-phenyl-N-p-acetylphenylnitrone
α-phenyl-N-p-acetyloxyphenylnitrone
α-phenyl-N-p-mercaptophenylnitrone
α-phenyl-N-p-acetylthiophenylnitrone
α-phenyl-N-p-methylthiophenylnitrone
α-phenyl-N-p-methylsulfinylphenylnitrone
α-phenyl-N-p-methylsulfonylphenylnitrone
α-phenyl-N-p-nitrophenylnitrone
α-phenyl-N-p-aminophenylnitrone
α-phenyl-N-p-cyclohexylphenylnitrone
α-phenyl-N-[p-(2-cyclohexenylphenyl)]nitrone
α-phenyl-N-p-biphenylnitrone
α-phenyl-N-[p-(2-thienylphenyl)]nitrone
α-phenyl-N-[p-(2-morpholinylphenyl)]nitrone
α-phenyl-N-(2-methyl-3-chlorophenyl)nitrone
α-phenyl-N-(2-methyl-4-chlorophenyl)nitrone
α-phenyl-N-(2-methyl-5-chlorophenyl)nitrone
α-phenyl-N-(2-methyl-6-chlorophenyl)nitrone
α-phenyl-N-(3-methyl-2-chlorophenyl)nitrone
α-phenyl-N-(3-methyl-4-chlorophenyl)nitrone
α-phenyl-N-(2-ethyl-4-chlorophenyl)nitrone
α-phenyl-N-(2-methyl-3-fluorophenyl)nitrone
α-phenyl-N-(2-methyl-4-fluorophenyl)nitrone
α-phenyl-N-(2-methyl-5-fluorophenyl)nitrone
α-phenyl-N-(2-methyl-6-fluorophenyl)nitrone
α-phenyl-N-(3-methyl-2-fluorophenyl)nitrone
α-phenyl-N-(3-methyl-4-fluorophenyl)nitrone
α-phenyl-N-(2-methyl-4-bromophenyl)nitrone
α-phenyl-N-(2-methyl-4-trifluoromethylphenyl)nitrone
α-phenyl-N-(2-methyl-4-methoxyphenyl)nitrone
α-phenyl-N-(2-methyl-4-hydroxyphenyl)nitrone
α-phenyl-N-(2-methyl-4-nitrophenyl)nitrone
α-phenyl-N-(2-methyl-4-ethylphenyl)nitrone
α-phenyl-N-(4-methyl-2-chlorophenyl)nitrone
α-phenyl-N-(4-methyl-3-chlorophenyl)nitrone
α-phenyl-N-(4-methyl-2-fluorophenyl)nitrone
α-phenyl-N-(4-methyl-3-fluorophenyl)nitrone
α-phenyl-N-(4-methyl-2-trifluoromethylphenyl)nitrone
α-phenyl-N-(4-methyl-3-trifluoromethylphenyl)nitrone
α-phenyl-N-(4-methyl-2-hydroxyphenyl)nitrone
α-phenyl-N-(4-methyl-3-hydroxyphenyl)nitrone
α-phenyl-N-(4-methyl-2-ethylphenyl)nitrone
α-phenyl-N-(2-chloro-4-bromophenyl)nitrone
α-phenyl-N-(2-chloro-4-fluorophenyl)nitrone
α-phenyl-N-(2-chloro-4-hydroxyphenyl)nitrone
α-phenyl-N-(2-chloro-4-methoxyphenyl)nitrone
α-phenyl-N-(2-chloro-4-nitrophenyl)nitrone
α-phenyl-N-(2-chloro-4-trifluoromethylphenyl)nitrone
α-phenyl-N-(2-chloro-4-ethylphenyl)nitrone
α-phenyl-N-(2-fluoro-5-methylphenyl)nitrone
α-phenyl-N-(2-fluoro-4-bromophenyl)nitrone
α-phenyl-N-(2-fluoro-4-hydroxyphenyl)nitrone
α-phenyl-N-(2-fluoro-4-methoxyphenyl)nitrone
α-phenyl-N-(2-fluoro-4-nitrophenyl)nitrone
α-phenyl-N-(2-fluoro-4-trifluoromethylphenyl)nitrone
α-phenyl-N-(2-fluoro-4-ethylphenyl)nitrone
α-phenyl-N-(2-hydroxy-4-nitrophenyl)nitrone
α-phenyl-N-(2-hydroxy-4-trifluoromethylphenyl)nitrone
α-o-chlorophenyl-N-o-chlorophenylnitrone
α-o-chlorophenyl-N-m-chlorophenylnitrone
α-o-chlorophenyl-N-p-chlorophenylnitrone
α-m-chlorophenyl-N-o-chlorophenylnitrone
α-m-chlorophenyl-N-m-chlorophenylnitrone
α-m-chlorophenyl-N-p-chlorophenylnitrone
α-p-chlorophenyl-N-o-chlorophenylnitrone
α-p-chlorophenyl-N-m-chlorophenylnitrone
α-p-chlorophenyl-N-p-chlorophenylnitrone
α-o-chlorophenyl-N-o-fluorophenylnitrone
α-o-chlorophenyl-N-m-fluorophenylnitrone
α-o-chlorophenyl-N-p-fluorophenylnitrone
α-m-chlorophenyl-N-o-fluorophenylnitrone
α-m-chlorophenyl-N-m-fluorophenylnitrone
α-m-chlorophenyl-N-p-fluorophenylnitrone
α-p-chlorophenyl-N-o-fluorophenylnitrone
α-p-chlorophenyl-N-m-fluorophenylnitrone
α-p-chlorophenyl-N-p-fluorophenylnitrone
α-o-chlorophenyl-N-o-methylphenylnitrone
α-o-chlorophenyl-N-m-methylphenylnitrone
α-o-chlorophenyl-N-p-methylphenylnitrone
α-m-chlorophenyl-N-o-methylphenylnitrone
α-m-chlorophenyl-N-m-methylphenylnitrone
α-m-chlorophenyl-N-p-methylphenylnitrone
α-p-chlorophenyl-N-o-methylphenylnitrone
α-p-chlorophenyl-N-m-methylphenylnitrone
α-p-chlorophenyl-N-p-methylphenylnitrone
α-o-chlorophenyl-N-o-trifluoromethylphenylnitrone
α-o-chlorophenyl-N-m-trifluoromethylphenylnitrone
α-o-chlorophenyl-N-p-trifluoromethylphenylnitrone
α-m-chlorophenyl-N-o-trifluoromethylphenylnitrone
α-m-chlorophenyl-N-m-trifluoromethylphenylnitrone
α-m-chlorophenyl-N-p-trifluoromethylphenylnitrone
α-p-chlorophenyl-N-o-trifluoromethylphenylnitrone
α-p-chlorophenyl-N-m-trifluoromethylphenylnitrone
α-p-chlorophenyl-N-p-trifluoromethylphenylnitrone
α-o-chlorophenyl-N-o-hydroxyphenylnitrone
α-o-chlorophenyl-N-m-hydroxyphenylnitrone
α-o-chlorophenyl-N-p-hydroxyphenylnitrone
α-m-chlorophenyl-N-o-hydroxyphenylnitrone
α-m-chlorophenyl-N-m-hydroxyphenylnitrone
α-m-chlorophenyl-N-p-hydroxyphenylnitrone
α-p-chlorophenyl-N-o-hydroxyphenylnitrone
α-p-chlorophenyl-N-m-hydroxyphenylnitrone
α-p-chlorophenyl-N-p-hydroxyphenylnitrone
α-o-fluorophenyl-N-o-fluorophenylnitrone
α-o-fluorophenyl-N-m-fluorophenylnitrone
α-o-fluorophenyl-N-p-fluorophenylnitrone
α-m-fluorophenyl-N-o-fluorophenylnitrone
α-m-fluorophenyl-N-m-fluorophenylnitrone
α-m-fluorophenyl-N-p-fluorophenylnitrone
α-p-fluorophenyl-N-o-fluorophenylnitrone
α-p-fluorophenyl-N-m-fluorophenylnitrone
α-p-fluorophenyl-N-p-fluorophenylnitrone
α-o-fluorophenyl-N-o-methylphenylnitrone
α-o-fluorophenyl-N-m-methylphenylnitrone
α-o-fluorophenyl-N-p-methylphenylnitrone
α-m-fluorophenyl-N-o-methylphenylnitrone
α-m-fluorophenyl-N-m-methylphenylnitrone
α-m-fluorophenyl-N-p-methylphenylnitrone α-p-fluorophenyl-N-o-methylphenylnitrone
α-p-fluorophenyl-N-m-methylphenylnitrone
α-p-fluorophenyl-N-p-methylphenylnitrone
α-o-fluorophenyl-N-o-trifluoromethylphenylnitrone
α-o-fluorophenyl-N-m-trifluoromethylphenylnitrone
α-o-fluorophenyl-N-p-trifluoromethylphenylnitrone
α-m-fluorophenyl-N-o-trifluoromethylphenylnitrone
α-m-fluorophenyl-N-m-trifluoromethylphenylnitrone
α-m-fluorophenyl-N-p-trifluoromethylphenylnitrone
α-p-fluorophenyl-N-o-trifluoromethylphenylnitrone
α-p-fluorophenyl-N-m-trifluoromethylphenylnitrone
α-p-fluorophenyl-N-p-trifluoromethylphenylnitrone
α-o-fluorophenyl-N-o-hydroxyphenylnitrone
α-o-fluorophenyl-N-m-hydroxyphenylnitrone
α-o-fluorophenyl-N-p-hydroxyphenylnitrone
α-m-fluorophenyl-N-o-hydroxyphenylnitrone
α-m-fluorophenyl-N-m-hydroxyphenylnitrone
α-m-fluorophenyl-N-p-hydroxyphenylnitrone
α-p-fluorophenyl-N-o-hydroxyphenylnitrone
α-p-fluorophenyl-N-m-hydroxyphenylnitrone
α-p-fluorophenyl-N-p-hydroxyphenylnitrone
α-o-methylphenyl-N-o-methylphenylnitrone
α-o-methylphenyl-N-m-methylphenylnitrone
α-o-methylphenyl-N-p-methylphenylnitrone
α-m-methylphenyl-N-o-methylphenylnitrone
α-m-methylphenyl-N-m-methylphenylnitrone
α-m-methylphenyl-N-p-methylphenylnitrone
α-p-methylphenyl-N-o-methylphenylnitrone
α-p-methylphenyl-N-m-methylphenylnitrone
α-p-methylphenyl-N-p-methylphenylnitrone
α-o-methylphenyl-N-o-trifluoromethylphenylnitrone
α-o-methylphenyl-N-m-trifluoromethylphenylnitrone
α-o-methylphenyl-N-p-trifluoromethylphenylnitrone
α-m-methylphenyl-N-o-trifluoromethylphenylnitrone
α-m-methylphenyl-N-m-trifluoromethylphenylnitrone
α-m-methylphenyl-N-p-trifluoromethylphenylnitrone
α-p-methylphenyl-N-o-trifluoromethylphenylnitrone
α-p-methylphenyl-N-m-trifluoromethylphenylnitrone
α-p-methylphenyl-N-p-trifluoromethylphenylnitrone
α-o-methylphenyl-N-o-hydroxyphenylnitrone
α-o-methylphenyl-N-m-hydroxyphenylnitrone
α-o-methylphenyl-N-p-hydroxyphenylnitrone
α-m-methylphenyl-N-o-hydroxyphenylnitrone
α-m-methylphenyl-N-m-hydroxyphenylnitrone
α-m-methylphenyl-N-p-hydroxyphenylnitrone
α-p-methylphenyl-N-o-hydroxyphenylnitrone
α-p-methylphenyl-N-m-hydroxyphenylnitrone
α-p-methylphenyl-N-p-hydroxyphenylnitrone
α-o-trifluoromethyl-N-o-trifluoromethylphenylnitrone
α-o-trifluoromethyl-N-m-trifluoromethylphenylnitrone
α-o-trifluoromethyl-N-p-trifluoromethylphenylnitrone
α-m-trifluoromethyl-N-o-trifluoromethylphenylnitrone
α-m-trifluoromethyl-N-m-trifluoromethylphenylnitrone
α-m-trifluoromethyl-N-p-trifluoromethylphenylnitrone
α-p-trifluoromethyl-N-o-trifluoromethylphenylnitrpne
α-p-trifluoromethyl-N-m-trifluoromethylphenylnitrone
α-p-trifluoromethyl-N-p-trifluoromethylphenylnitrone
α-o-trifluoromethyl-N-o-hydroxyphenylnitrone
α-o-trifluoromethyl-N-m-hydroxyphenylnitrone
α-o-trifluoromethyl-N-p-hydroxyphenylnitrone
α-m-trifluoromethyl-N-o-hydroxyphenylnitrone
α-m-trifluoromethyl-N-m-hydroxyphenylnitrone
α-m-trifluoromethyl-N-p-hydroxyphenylnitrone
α-p-trifluoromethyl-N-o-hydroxyphenylnitrone
αp-trifluoromethyl-N-m-hydroxyphenylnitrone
α-p-trifluoromethyl-N-p-hydroxyphenylnitrone
α-o-hydroxyphenyl-N-o-hydroxyphenylnitrone
α-o-hydroxyphenyl-N-m-hydroxyphenylnitrone
α-o-hydroxyphenyl-N-p-hydroxyphenylnitrone
α-m-hydroxyphenyl-N-o-hydroxyphenylnitrone
α-m-hydroxyphenyl-N-m-hydroxyphenylnitrone
α-m-hydroxyphenyl-N-p-hydroxyphenylnitrone
α-p-hydroxyphenyl-N-o-hydroxyphenylnitrone
α-p-hydroxyphenyl-N-m-hydroxyphenylnitrone
α-p-hydroxyphenyl-N-p-hydroxyphenylnitrone
α-p-chlorophenyl-N-p-nitrophenylnitrone
α-p-chlorophenyl-N-p-cyanophenylnitrone
α-p-chlorophenyl-N-p-aminophenylnitrone
α-p-chlorophenyl-N-p-trifluoromethoxyphenylnitrone
α-p-chlorophenyl-N-p-methoxyphenylnitrone
α-p-chlorophenyl-N-p-ethoxyphenylnitrone
α-p-chlorophenyl-N-p-acetylphenylnitrone
α-p-chlorophenyl-N-p-acetyloxyphenylnitrone
α-p-chlorophenyl-N-p-benzyloxyphenylnitrone
α-p-chlorophenyl-N-p-mercaptophenylnitrone
α-p-chlorophenyl-N-p-acetylthiophenylnitrone
α-p-chlorophenyl-N-p-methylthiophenylnitrone
α-p-chlorophenyl-N-p-methylsulfinylphenylnitrone
α-p-chlorophenyl-N-p-methylsulfonylphenylnitrone
α-p-chlorophenyl-N-p-biphenylnitrone
α-p-chlorophenyl-N-(2,3-dimethylphenyl)nitrone
α-p-chlorophenyl-N-(2,4-dimethylphenyl)nitrone
α-p-chlorophenyl-N-(2,5-dimethylphenyl)nitrone
α-p-chlorophenyl-N-(2,6-dimethylphenyl)nitrone
α-p-chlorophenyl-N-(3,4-dimethylphenyl)nitrone
α-p-chlorophenyl-N-(3,5-dimethylphenyl)nitrone
α-p-chlorophenyl-N-(2,3-dichlorophenyl)nitrone
α-p-chlorophenyl-N-(2,4-dichlorophenyl)nitrone
α-p-chlorophenyl-N-(2.5-dichlorophenyl)nitrone
α-p-chlorophenyl-N-(2,6-dichlorophenyl)nitrone
α-p-chlorophenyl-N-(3,4-dichloropheny)nitrone
α-p-chlorophenyl-N-(3,5-dichlorophenyl)nitrone
α-p-chlorophenyl-N-(2-methyl-3-chlorophenyl)nitrone
α-p-chlorophenyl-N-(2-methyl-4-chlorophenyl)nitrone
α-p-chlorophenyl-N-(3-methyl-2-chlorophenyl)nitrone
α-p-chlorophenyl-N-(2-methyl-3-fluorophenyl)nitrone
α-p-chlorophenyl-N-(2-methyl-4-fluorophenyl)nitrone
α-p-chlorophenyl-N-(3-methyl-2-fluorophenyl)nitrone
α-p-chlorophenyl-N-(2-methyl-3-hydroxyphenyl)nitrone
α-p- chlorophenyl-N-(2-methyl-4-hydroxyphenyl)nitrone
α-p-chlorophenyl-N-(3-methyl-2-hydroxyphenyl)nitrone α-p-chlorophenyl-N-(2-chloro-4-methylphenyl)nitrone
α-p-chlorophenyl-N-(2-chloro-4-ethylphenyl)nitrone
α-p-chlorophenyl-N-(3-chloro-2-ethylphenyl)nitrone
α-p-chlorohenyl-N-(2-chloro-3-fluorophenyl)nitrone
α-p-chlorophenyl-N-(2-chloro-4-fluorophenyl)nitrone
α-p-chlorophenyl-N-(3-chloro-2-fluorophenyl)nitrone
α-p-chlorophenyl-N-(2-fluoro-3-hydroxyphenyl)nitrone
α-p-chlorophenyl-N-(2-fluoro-4-hydroxyphenyl)nitrone
α-p-chlorophenyl-N-(3-fluoro-2-hydroxyphenyl)nitrone
α-p-chlorophenyl-N-(2,3-difluorophenyl)nitrone
α-p-chlorophenyl-N-(2,4-difluorophenyl)nitrone
α-p-chlorophenyl-N-(2,5-difluorophenyl)nitrone
α-p-chlorophenyl-N-(2,6-difluorophenyl)nitrone
α-p-chlorophenyl-N-(3,4-difluorophenyl)nitrone
α-p-chlorophenyl-N-(3,5-difluorophenyl)nitrone
α(2-methyl-3-chlorophenyl)-N-o-chlorophenylnitrone
α-(2-methyl-3-chlorophenyl)-N-m-chlorophenylnitrone
α-(2-methyl-3-chlorophenyl)-N-p-chlorophenylnitrone
α-(2-methyl-3-chlorophenyl)-N-o-fluorophenylnitrone
α-(2-methyl-3-chlorophenyl)-N-m-fluorophenylnitrone
α-(2-methyl-3-chlorophenyl)-N-p-fluorophenylnitrone
α-(2-methyl-3-chlorophenyl)-N-o-methylphenylnitrone
α-(2-methyl-3-chlorophenyl)-N-m-methylphenylnitrone
α-(2-methyl-3-chlorophenyl)-N-p-methylphenylnitrone
α-(2-methyl-3-chlorophenyl)-N-o-trifluoromethylphenylnitrone
α-(2-methyl-3-chlorophenyl)-N-m-trifluoromethylphenylnitrone
α-(2-methyl-3-chlorophenyl)-N-p-trifluoromethylphenylnitrone
α-(2-methyl-3-chlorophenyl)-N-o-hydroxyphenylnitrone
α-(2-methyl-3-chlorophenyl)-N-m-hydroxyphenylnitrone
α-(2-methyl-3-chlorophenyl)-N-p-hydroxyphenylnitrone
α-(2-methyl-4-chlorophenyl)-N-o-chlorophenylnitrone
α-(2-methyl-4-chlorophenyl)-N-m-chlorophenylnitrone
α-(2-methyl-4-chlorophenyl)-N-p-chlorophenylnitrone
α-(2-methyl-4-chlorophenyl)-N-o-fluorophenylnitrone
α-(2-methyl-4-chlorophenyl)-N-m-fluorophenylnitrone
α-(2-methyl-4-chlorophenyl)-N-p-fluorophenylnitrone
α-(2-methyl-4-chlorophenyl)-N-o-methylphenylnitrone
α(2-methyl-4-chlorophenyl)-N-m-methylphenylnitrone
α-(2-methyl-4-chlorophenyl)-N-p-methylphenylnitrone
α-(2-methyl-4-chlorophenyl)-N-o-trifluoromethylphenylnitrone
α-(2-methyl-4-chlorophenyl)-N-m-trifluoromethylphenylnitrone
α-(2-methyl-4-chlorophenyl)-N-p-trifluoromethylphenylnitrone
α-(2-methyl-4-chlorophenyl)-N-o-hydroxyphenylnitrone
α-(2-methyl-4-chlorophenyl)-N-m-hydroxyphenylnitrone
α-(2-methyl-4-chlorophenyl)-N-p-hydroxyphenylnitrone
α-(2-methyl-3-chlorophenyl)-N-(2,3-dimethylphenyl)nitrone
α-(2-chloro-4-fluorophenyl)-N-m-fluorophenylnitrone
α-(2-chloro-4-methoxyphenyl)-N-(2-chloro-4-fluorophenyl)nitrone
α(o-chloro-4-methoxyphenyl)-N-(2,4,6-trifluorophenyl)nitrone
α-(p-chloro-4-methoxyphenyl)-N-(2-chloro-5-methylphenyl)nitrone
α(p-fluoro-4-methoxyphenyl)-N-(3,4-dihydroxyphenyl)nitrone
α-(3,4-dihydroxy-4
α-(3,4-dihydroxy-4-methoxyphenyl)-N-(o-fluorophenyl)nitrone

EXAMPLE 11

A cream was prepared as follows:

| | |
|---|---|
| α-Phenyl-N-p-chlorophenylnitrone | 0.5 g. |
| Titanium oxide | 10 g. |
| Red iron oxide | 0.3 g. |
| Yellow iron oxide | 0.2 g. |
| Brown iron oxide | 0.4 g. |
| Chestnut iron oxide | 0.2 g. |

Several stearyl alcohols oxyethylenated with 33 mols. of:

| | |
|---|---|
| Ethylene oxide | 7 g. |
| Propyl parahydroxybenzoate | 0.2 g. |
| Polyglycol stearate | 6 g. |
| Water, Q.S.P. | 100 g. |

Other creams identical to that described immediately above are prepared by replacing α-phenyl-N-p-chlorophenylnitrone with any of the previously mentioned nitrone compounds.

EXAMPLE 12

A dermatological cleansing cake is prepared by mixing together the following components:

| | |
|---|---|
| Esters of sodium isothionate and coprafatty acids (sold under the tradename "IGEPON A" having the formula R—COO—CH$_2$—CH$_2$—SO$_3$—Na, wherein R equals fatty acid derivatives having 12-15 carbon atoms) | 75 g. |
| Lanolin derivatives | 22.75 g. |
| α-p-fluorophenyl-N-phenylnitrone | 0.75 g. |

Other dermatological cleansing cakes, identical to the above, are prepared by replacing α-p-fluorophenyl-N- phenylnitrone with any one of the aforementioned active compounds.

EXAMPLE 13

A powder comprising the following mixture:

| Talc | 99.6 g. |
|---|---|
| Glycerine oleate | 3.0 g. |
| Isopropyl myristate | 7.0 g. |
| α-(2,6-dimethylphenyl)-N-phenylnitrone | 0.5 g. |
| Perfume | 2 cc. |

Other equally effective powder compositions identical to the above are prepared except that the active ingredient α-(2,6-dimethylphenyl)-N-phenylnitrone is replaced by any of the other aforementioned active compounds.

EXAMPLE 14

An anti-inflammatory composition in milk form having the following composition:

| Ingredient | Weight in grams |
|---|---|
| Hydrogenated, ethoxylate (10 mol.) lanolin | 1.8 |
| Triglyceride of fatty acid of coconut | 7.0 |
| Cetylalcohol | 0.6 |
| Stearylalcohol | 0.6 |
| Paraffin oil (lightweight) | 5.0 |
| α-phenyl-N-(2,4-difluorophenyl) nitrone | 0.75 |
| Stearic acid | 3.0 |
| Demineralized water | 72.2 |
| Triethanolamine | 0.8 |
| Perfume | 0.5 |
| Carboxyvinylpolymer | 2.0 |
| Conservation agent | 2.0 | was manufactured as follows:

A mixture of 1.8 g. hydrogenated, ethoxylated (10 mol.) lanolin, 7.0 g. triglyceride of fatty acid of coconut, 0.6 g. cetylalcohol, 0.6 g. stearyl alcohol, 5.0 g. paraffin oil, 0.05 g. hydrocortisone and 3.0 g. of stearic was blended at 70° C. After addition of 0.75 g. α-phenyl-N-(2,4-difluorophenyl)nitrone, 2.0 g. carboxyvinylpolymer in 72.2 g. demineralized water was added at 70° C. with stirring to the resulting suspension. The mixture was stirred for 15 minutes and then cooled. 0.8 g. of triethanolamine and 0.5 g. of perfume were added at 60° C. and 45° C. respectively. The resulting mixture was stirred until cold and a white milk, which was stable at 3,000 Rpm for one hour was obtained. Viscosity: 6000 Cp (Brockfield, Spindel, 5, 10 Rpm).

EXAMPLE 15

0.5 g. of α-p-chlorophenyl-N-p-fluorophenylnitrone and 0.20 g. α-p-chlorophenyl-N-phenylnitrone are predispersed in 30.0 g. of propylene glycol. The mixture is then homogenized into 97.4 grams of finished cream, ointment or lotion following a modification of any one of the procedures described in F. W. Martin et al, "Remington's Pharmaceutical Sciences", 14th Ed., Mack Publishing Co., Easton, Pennsylvania 1965.

We claim:

1. A method of treating inflammation in warm-blooded animals comprising the topical administration to said animal of an effective amount of a pharmaceutically-active compound of the formula:

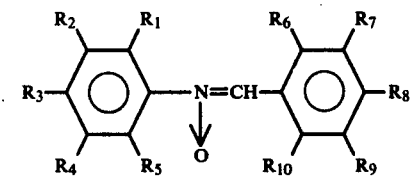

where:
$R_1$, $R_2$, $R_3$, $R_4$, $R_5$, $R_6$, $R_7$, $R_8$, $R_9$ and $R_{10}$ may be the same or different and are:
hydrogen,
alkyl,
cyano,
nitro,
amino,
haloloweralkoxy,
haloloweralkyl,
halo,
loweralkoxy and
hydroxy.

2. The method of topically treating inflammation according to claim 1 where the compound administered is α-phenyl-N-p-chlorophenylnitrone.

3. The method of topically treating inflammation according to claim 1 where the compound administered is α-4-biphenyl-N-4-chlorophenylnitrone.

4. The method of topically treating inflammation according to claim 1 where the compound administered is α-2-chlorophenyl-N-3-chloro-2-methylphenylnitrone.

* * * * *

UNITED STATES PATENT AND TRADEMARK OFFICE
CERTIFICATE OF CORRECTION

PATENT NO. : 4,153,722
DATED : May 8, 1979
INVENTOR(S) : Henry Flud Campbell et al It is certified that error appears in the above-identified patent and that said Letters Patent are hereby corrected as shown below:

Column 1, line 50, change "Rhd 3" to--$R_3$--

Column 2, line 16, change "$R_g$"--$R_9$-- line 62, after "zinyl" insert--,--

Column 3, line 8, change "αhalophenyl-N-hydroxyphenylnitrone" to--α-halophenyl-N-hydroxyphenylnitrone--

Column 7, line 58, change "p-cyclohexylideneaniline" to--p-cyclohexylbenzylideneaniline--

Column 10, line 30, delete "2-fluor-4-methylphenylhydroxylamine"

Column 13, line 42, change "α(3-methyl-4-chlorophenyl)-N-phenylnitrone" to--α-(3-methyl-4-chlorophenyl)-N-phenylnitrone--

Column 17, line 68, change "nitrpne" to--nitrone--

Column 18, line 12, change "αp-trifluoromethyl-N-m-hydroxyphenylnitrone" to--α-p-trifluoromethyl-N-m-hydroxyphenylnitrone-- line 49, change "α-p-chlorophenyl-N-(3,4-dichloropheny)nitrone" to--α-p-chlorophenyl-N-(3,4-dichlorophenyl)nitrone--

Column 19, line 22, change "α(2-methyl-3-chlorophenyl)-N-o-chlorophenylni-" to--α-(2-methyl-3-chlorophenyl)-N-o-chlorophenylni- -- line 67, change "α(2-methyl-4-chlorophenyl)-N-m-methylphenylni-" to--α-(2-methyl-4-chlorophenyl)-

UNITED STATES PATENT AND TRADEMARK OFFICE
CERTIFICATE OF CORRECTION

PATENT NO. : 4,153,722
DATED : May 8, 1979
INVENTOR(S) : Henry Flud Campbell et al It is certified that error appears in the above-identified patent and that said Letters Patent are hereby corrected as shown below:

N-m-methylphenylni- --

Column 20, line 21, change "α(o-chloro-4-methoxyphenyl)-N-(2,4,6-trifluoro-" to --α-(o-chloro-4-methoxyphenyl)-N-(2,4,6-trifluoro- -- line 27, change "α-(3,4-dihydroxy-4" to --α-(3,4-dihydroxy-4-methoxyphenyl)-N-(p-fluorophenyl)-nitrone--

Signed and Sealed this

Twenty-seventh Day of November 1979

[SEAL]

Attest:

RUTH C. MASON
Attesting Officer

LUTRELLE F. PARKER
Acting Commissioner of Patents and Trademarks